United States Patent [19]
Micklish

[11] Patent Number: 5,285,682
[45] Date of Patent: Feb. 15, 1994

[54] SPONGE ABSORBED FLUID MEASURING UNIT

[76] Inventor: Clara J. Micklish, 13303 Birch Grove Dr., Houston, Tex. 77083

[21] Appl. No.: 17,971

[22] Filed: Feb. 12, 1993

Related U.S. Application Data

[63] Continuation of Ser. No. 682,475, Apr. 9, 1991, abandoned.

[51] Int. Cl.⁵ .................. G01F 22/00; G01G 5/04
[52] U.S. Cl. ............................. 73/149; 177/208
[58] Field of Search ............. 73/149, 866, 865.9, 73/38, 747, 749, 751, 865, 862.471, 862.454; 177/208, 209, 50; 141/83; 206/363, 459.1, 459.5, 370, 438; 128/767, 771; 210/85, 94, 95

[56] References Cited

U.S. PATENT DOCUMENTS

| | | | |
|---|---|---|---|
| 302,402 | 7/1884 | Herndon | 177/208 |
| 1,524,928 | 2/1925 | Hordel et al. | 177/50 X |
| 2,462,820 | 2/1949 | Wallace | 73/747 |
| 2,706,908 | 4/1955 | MacRoberts | 73/149 |
| 3,378,090 | 4/1968 | Christie | 177/208 X |
| 4,422,548 | 12/1983 | Cheesman et al. | 206/370 |
| 4,429,789 | 2/1984 | Pucket, Jr. | 206/370 |
| 4,478,332 | 10/1984 | Wiestmiller | 206/361 |
| 4,562,842 | 1/1986 | Morfeld et al. | 73/434 X |

FOREIGN PATENT DOCUMENTS

| | | | |
|---|---|---|---|
| 233181 | 2/1986 | Fed. Rep. of Germany | 73/149 |
| 2308091 | 12/1976 | France | 177/208 |
| 505483 | 2/1956 | Italy | 177/208 |

*Primary Examiner*—Thomas P. Noland
*Attorney, Agent, or Firm*—Pravel, Hewitt, Kimball & Krieger

[57] ABSTRACT

A device for measuring the amount of fluids absorbed by surgical sponges. The sponges are placed in a receiving cylinder. A flexible diaphragm at the bottom of the cylinder flexes or deflects from the weight. This deflection displaces a fluid in a base unit. The fluid is displaced into a graduated cylinder. The cylinder is graduated in simple volume units or can include compensation for the sponge weights. A counter is included which allows the number of sponges being measured to be counted.

14 Claims, 1 Drawing Sheet

SPONGE ABSORBED FLUID MEASURING UNIT

This is a continuation of co-pending application Ser. No. 07/682,475, filed on Apr. 9, 1991, and now abandoned.

BACKGROUND OF THE INVENTION

1. Field of the Invention

The invention relates to the measurement of fluids absorbed in surgical sponges.

2. Description of the Related Art

Various sponges are used during surgical procedures to absorb blood and other fluids utilized during the operation. One problem which occurs is that the amount of blood lost during the procedure must be tracked. Some of the blood is suctioned direction into a graduated cylinder for measurement, but some blood is always lost under the various drapes and on the floor and some blood is absorbed in the sponges used during the procedure. Some estimate of the blood absorbed by the sponges thus needs to be made. Conventionally the estimate is made merely by a visual inspection of the sponges, but this technique is highly prone to error. In some instances the absorbed blood estimate is more important, such as in critically ill patients, children and patients being evaluated for blood transfusion therapy. In these instances the sponges are individually weighed. However, this conventionally is a tedious process. Additionally, because the scale used in weighing the sponges produces a weight reading, calculations must be performed to translate the weight to a volume measurement, introducing an additional error location. Thus it is relatively common that only very rough estimates, or even in some cases, no track at all, is kept of the blood absorbed by the sponge.

SUMMARY OF THE INVENTION

The present invention is a device for simply and quickly determining the amount of fluid absorbed by sponges during a surgical procedure. A base unit contains two projecting cylinders. One cylinder is of a large diameter and includes at its bottom a flexible diaphragm. The second cylinder is relatively thin and tall and is graduated. Both units are placed on the base, which is then filled with water or other fluid up to a zero level graduation. The fluid containing sponges are placed in the larger cylinder and the diaphragm flexes. When the diaphragm flexes, fluid is displaced upwardly in the graduated cylinder. The graduations indicate the volume of fluid absorbed by the sponge. The cylinder can either be graduated for a particular size sponge, in which case the graduations can be made to compensate for the weight of the sponges, or multiple size units can be developed, in which case graduations can be quite complex if the weight of the sponge is taken into account or can be more simple by measuring the total weight and ignoring the weight of the sponges. The device does not have to be sterilized often because a disposable plastic liner is used in the large receiving cylinder so that the sponges do not contact the actual device. Further, the plastic linear can be readily disposed of after simple removal. Clean-up of the device is simplified because the device is preferably formed of several pieces which can be taken apart. Operation is thus quick and easy because the sponges are merely placed in the large cylinder and the weight of the absorbed fluids read off of the graduations.

Preferably a counter is also included with the device so that a count of the sponges placed in the large cylinder can be maintained. The counter is preferably a simple mechanical counter which increments upon depression of one button and is cleared on the depression of the second button. However, a variation includes a lever operated counter wherein the lever protrudes and extends over the large cylinder so that the count is made automatically as the sponge is deposited. A simple button is used to clear this counter.

BRIEF DESCRIPTION OF THE DRAWINGS

A better understanding of the present invention can be obtained when the following detailed description of the preferred embodiment is considered injunction with the following drawings, in which.

DETAILED DESCRIPTION OF THE PREFERRED EMBODIMENT

Figure 1:
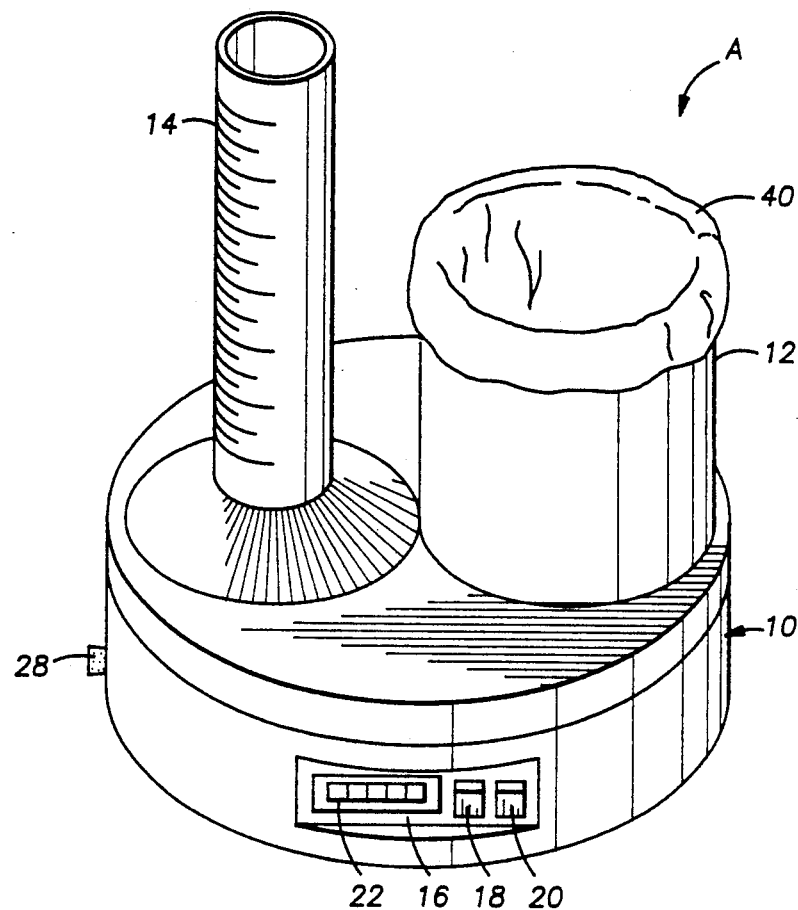
FIG. 1 is a perspective view of an apparatus according the present invention.

The present invention is an apparatus for easily and quickly determining the weight and thus volume of fluids absorbed by surgical sponges. The apparatus, generally referred to by the letter A, includes a base portion 10, a large receiving cylinder 12 and a thin graduated cylinder 14. The cylinders 12 and 14 are placed over the base 10. While the cylinders 12 and 14 are shown utilizing a circular cross section, it is understood that other shapes could be used, such as various rectangular profiles. Use of rectangular profiles for the base 10 and the cylinders 12 and 14 could allow a smaller size for the apparatus A.

Preferably located and attached to the base 10 is a counter 16. Preferably the counter 16 includes an increment button 18, a clear button 20 and a display 22. Depressing the count or increment button 18 increases the count displayed in the counter display 22. Thus the increment button 18 is depressed each time a sponge is placed in the receiving cylinder 12. Depressing the clear button 20 is done after the surgical procedure is completed and the reading has been recorded or prior to the commencement of a procedure. The counter 16 thus provides a count to keep track of the number of sponges being weighed.

Figure 2:
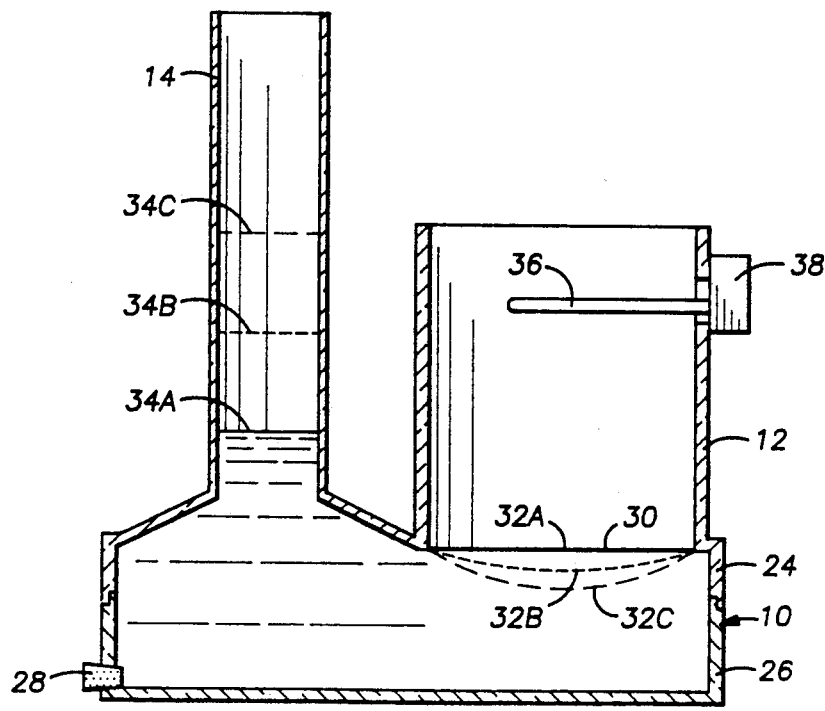
FIG. 2 is a cross-sectional view of the apparatus of FIG. 1.

As shown in FIG. 2, the base 10 preferably contains two portions, an upper portion 24 and a lower portion 26. Preferably the lower portion 26 contains a port or tap 28 to allow a small amount of fluid to be drained if desired. The upper and lower portions 24 and 26 are preferably well sealed when mated so that the fluid does not leak. Two portions 24 and 26 are provided so that the base 10 can be easily split to simplify cleaning. The cylinders 12 and 14 are attached to the upper portion 24. The upper portion 24 preferably is slightly raised in the area where the graduated cylinder 14 is located to allow an inherent liquid seal to develop in the base 10 as it is filled with fluid through the graduated cylinder 14.

The receiving cylinder 12 contains a flexible diaphragm 30 formed of a suitable plastic or other flexible material at its bottom end. The upper portion 24 of the base 10 is open throughout the interior inner diameter of the receiving cylinder 12 so that the flexible diaphragm 30 can flex and depress into the base 10. The opening between the base 10 and the graduated cylinder 14 is completely open. Preferably the base 10 is filled with water or other fluid through the graduated cylinder 14. The graduated cylinder 14 contains a zero point graduation so that the base 10 and graduated cylinder 14 are filled until the fluid reaches this reference point. Should too much fluid be supplied, the port 28 is utilized to lower the fluid level.

A disposable plastic liner 40 is preferably placed in the receiving cylinder 12, much like a plastic garbage bag. The plastic liner 40 helps keep the apparatus A sterile and provides a means to readily dispose of the sponges after the readings are made. The plastic liner 40 is sufficiently thin as to not interfere with the flexing of the diaphragm 30 and the measurements.

The base 10, receiving cylinder 12, graduated cylinder 14, counter 16, diaphragm 30 and port 28 are made of materials which can be readily cleaned using conventional techniques without resulting in a degradation of the materials. It is preferred that various plastics be utilized. The graduated cylinder 14 is preferably a transparent or translucent material to allow easy reading of the fluid level. The base 10 can be transparent to allow confirmation of a liquid seal and the receiving cylinder 12 can be transparent to allow simpler viewing of the deposited materials. The diaphragm 30 can be attached to the base 10 or the receiving cylinder 12, but preferably it is replaceably connected so that the diaphragm 30 can be replaced as it ages or stretches. The specific attachment means is not illustrated in the drawings, suitable means being within the knowledge of those skilled in the art.

As sponges are placed in the receiving cylinder 12, the diaphragm 30 flexes and moves into the base 10. This is shown by the three positions of the diaphragm noted as 32A, 32B and 32C. Position 32A represents the zero sponge or empty position, with a corresponding graduation level of 34A on the graduated cylinder 14. This is the zero reference level to which the apparatus A is filled with fluid. As sponges are placed in the receiving cylinder 12, the increment button 18 is depressed and the counter 16 is incremented. The weight of the sponges and the absorbed fluids causes the diaphragm 30 to travel to position 32B. This intrusion of the diaphragm 30 into the base 10 displaces the fluid contained in the base 10 upwardly into the graduated cylinder 14, so that the fluid level in the cylinder 14 now reaches level 34B. Adding additional sponges deflects the diaphragm 30 to position 32C, with a resulting increase of fluid contained in the graduated cylinder 14 to a level indicated by 34C. Thus as sponges are placed in the receiving cylinder 12, fluid rises in the graduated cylinder 14. The diaphragm 30 is sufficiently flexible so that even relatively small sponges being placed in the receiving cylinder 12 cause it to deflect. Yet the diaphragm 30 is sufficiently inflexible to allow a relatively large number of sponges to be placed. Variations in the flexibility of the diaphragm used allows for different models which have capacities for different amounts and sizes of sponges.

The graduations located on or inscribed in the graduated cylinder 14 vary depending upon the particular use for the particular apparatus A. In the simplest embodiment, the graduations simply indicate the total fluid volume contained in the receiving cylinder 12. The level is developed because of the weight of the fluid and sponges deflecting the diaphragm 30, thus causing the fluid to flow up the graduated cylinder 14. Because of the elasticity of the diaphragm 30, each unit weight will cause a predetermined amount of fluid to enter the graduated cylinder 14. For the accuracy required in this application, a simple approximation of the weight of the received materials to an equivalent room temperature water volume is satisfactory. Blood has a weight per unit volume not overly dissimilar from water and the remaining absorbed fluids are generally water-based solutions. Thus the weight can be simply converted to a volume. The actual height in the graduated cylinder 14 of the displayed fluid depends on the size of the receiving cylinder 12, the flexibility of the diaphragm 30 and the diameter of the graduated cylinder 14. If relatively low volumes of fluids are to be measured, then the graduating cylinder 14 is preferably thinner, to provide more accuracy for the smaller amount to be measured, while with a greater amount of fluid is to measured, as in using larger sponges, the graduated cylinder 14 is preferably slightly larger in diameter so that a given weight does not cause fluids to rise in the graduated cylinder 14 as quickly. It is noted that in this simple embodiment the graduations are basically linear and correspond directly to the total weight of the items placed in the receiving cylinder 12. At a given approximation level this is considered sufficiently accurate because the sponges contribute very little to the total weight, generally being a simple coarse, thin fabric mesh, with the absorbed fluid quickly outweighing the sponge. This particular simple embodiment allows multiple sizes of sponges to be weighed with the particular apparatus A.

If greater accuracy is desired, the graduations on the cylinder 14 are calibrated for particular sponge sizes, thus rendering the apparatus A differently calibrated for each particular sponge size. As an alternative, the counter 16 could indicate effective total sponge volume for the particular sponge size as well as the sponge count. This value could be simply subtracted from the total volume value. In these two variations, different versions of the apparatus A are required for different sponge sizes. Yet another alternative and more complex calibration scheme could be utilized to compensate for the various sizes and types of sponges utilized on a single graduated cylinder 14, but this is considered to be sufficiently complex that either multiple units for different size sponges or the simple total volume measurement graduations are preferred.

Additionally, instead of the simple counter 16 located on the base 10 which requires manual operation for counting, an arm or lever 36 could be placed over the top opening of the receiving cylinder 12 so that as a sponge is placed or tossed into the receiving cylinder 12, the lever 36 actuates the counter 38, thus automatically incrementing the count. A separate button (not shown) would be utilized to clear the counter 38.

Thus is shown a simple, fast device for measuring the fluids absorbed by surgical sponges has been described. Clean-up procedures are greatly simplified and no time consuming balance beam measurements and calculations need to be taken or made. The sponges are simply placed in the receiving cylinder 12, resulting in an absorbed volume indication which is read from the graduated cylinder 14.

Having described the invention above, various modifications of the techniques, procedures, material and equipment will be apparent to those in the art. It is intended that all such variations within the scope and spirit of the appended claims be embraced thereby.

I claim:

1. A apparatus for measuring fluid volumes absorbed in a particular type of article, comprising:

a base unit having top, bottom and side surfaces, said top surface having two openings;

a fluid filling said base unit;

a receiving chamber having open top and bottom surfaces and located over a first of said base unit top surface openings the first top opening for receiving articles of the particular type to measure;

a graduated chamber having open top and bottom surfaces and located over the second of said base unit top surface openings, said graduated chamber having graduations indicating quantities of the fluid volume absorbed in the articles placed in said receiving chamber; and a flexible diaphragm positioned at said first base unit top surface opening and deflecting towards said base unit bottom surface when articles to be measured are placed in said receiving chamber, thereby displacing said fluid located in said base unit from said base unit into said graduated chamber 2. The apparatus of claim 1,
wherein said base unit top surface is multi-level and the second opening therein is raised with respect to said first opening therein.

3. The apparatus of claim 1,
wherein said base unit includes a port for releasing fluid.

4. The apparatus of claim 1,
wherein said base unit is formed by a plurality of pieces.

5. The apparatus of claim 1, further comprising:
means mounted to the apparatus for counting the number of articles being measured.

6. The apparatus of claim 5,
wherein said counting means comprises a counter having a control for manual manipulation to increase the count and a control for resetting said counter.

7. The apparatus of claim 5,
wherein said counting means comprises means located in said receiving chamber for counting the articles placed in said receiving chamber and means for resetting the count.

8. The apparatus of claim 1,
wherein said graduated chamber is translucent.

9. The apparatus of claim 1,
wherein said graduated chamber is transparent.

10. An apparatus for measuring fluid volumes absorbed in a particular type of article, comprising:
a base unit having top, bottom and side surfaces, said top surface having two openings;
a fluid filling said base unit;
a receiving chamber having open top and bottom surfaces and located over a first of said base unit top surface openings, the first top opening for receiving articles to be measured;
a graduated chamber having open top and bottom surfaces and located over the second of said base unit top surface openings, said graduated chamber having graduations indicating quantities of the fluid volume absorbed in the articles placed in said receiving chamber; and
a flexible diaphragm positioned at said first base unit top surface opening and deflecting towards said base unit bottom surface when articles to be measured are placed in said receiving chamber, thereby displacing said fluid located in said base unit from said base unit into said graduated chamber,
wherein said graduated chamber graduations include corrections for the dry weight of the articles being measured.

11. An apparatus for measuring fluid volumes absorbed in a particular type of articles, comprising:
a receiving chamber having open top and bottom surfaces, the top opening for receiving articles of the particular type to be measured;
a flexible diaphragm positioned at the bottom opening of said receiving chamber and deflecting downwards away from said receiving chamber when articles to be measured are placed in said receiving chamber;
a graduated chamber having open top and bottom surfaces, said graduated chamber having graduations indicating quantities of the fluid volume absorbed in the articles placed in said receiving chamber;
a base unit having top, bottom and side surfaces, said base unit having means for receiving said receiving chamber, said graduated chamber and said flexible diaphragm at the top surface thereof and allowing fluid communication between said flexible diaphragm and said graduated chamber; and
a fluid filling said base unit, wherein when articles are placed in said receiving chamber, fluid is displaced into said graduated chamber as said flexible diaphragm deflects.

12. The apparatus of claim 11, wherein the graduated chamber graduations include corrections for the dry weight of the articles being measured.

13. An apparatus for measuring fluid volumes absorbed in a particular type of article, comprising:
a receiving chamber having open top and bottom surfaces, the top opening for receiving articles in the particular type to be measured;
a flexible diaphragm positioned at the bottom opening of said receiving chamber and deflecting downwards away from said receiving chamber when articles to be measured are placed in said receiving chamber;
a graduated chamber having open top and bottom surfaces, said graduated chamber having graduations indicating quantities of the fluid volume absorbed in the articles placed in said receiving chamber;
means connected to said bottom opening of said receiving chamber at said flexible diaphragm and to the bottom opening of said graduated chamber for allowing fluid communication between said receiving chamber and said graduated chamber; and
fluid filling said means for allowing fluid communication, wherein when articles are placed in said receiving chamber, fluid is displaced into said graduated chamber as said flexible diaphragm deflects.

14. The apparatus of claim 13, wherein the graduated chamber graduations include corrections for the dry weight of the articles being measured.

* * * * *